(12) United States Patent
Nazari

(10) Patent No.: US 10,517,687 B2
(45) Date of Patent: *Dec. 31, 2019

(54) THERAPEUTIC SKIN LIFTING DEVICE AND RELATED SYSTEMS AND METHODS

(71) Applicant: CARPAL AID, LLC, Chatsworth, CA (US)

(72) Inventor: Joseph Nazari, Glendale, CA (US)

(73) Assignee: CARPAL AID, LLC, Chatsworth, CA (US)

( * ) Notice: Subject to any disclaimer, the term of this patent is extended or adjusted under 35 U.S.C. 154(b) by 604 days.

This patent is subject to a terminal disclaimer.

(21) Appl. No.: 15/067,132

(22) Filed: Mar. 10, 2016

(65) Prior Publication Data

US 2016/0193005 A1 Jul. 7, 2016

Related U.S. Application Data

(63) Continuation-in-part of application No. 13/825,759, filed as application No. PCT/US2013/028099 on Feb. 27, 2013, now Pat. No. 9,314,312.

(Continued)

(51) Int. Cl.
*A61H 1/00* (2006.01)
*A61F 13/10* (2006.01)
(Continued)

(52) U.S. Cl.
CPC .............. *A61B 90/02* (2016.02); *A61B 90/60* (2016.02); *A61F 5/0118* (2013.01);
(Continued)

(58) Field of Classification Search
CPC ........ A61B 90/02; A61F 5/0118; A61F 13/02; A61F 13/0273; A61F 13/0276; A61F 13/10; A61F 13/0118

See application file for complete search history.

(56) References Cited

U.S. PATENT DOCUMENTS 1,612,267 A * 12/1926 Dickson .............. A61F 13/0203
206/441
3,971,374 A * 7/1976 Wagner ................. A61F 13/104
602/58

(Continued)

FOREIGN PATENT DOCUMENTS

CN 1714767 A 1/2006
EP 1604625 A1 12/2005
(Continued)

OTHER PUBLICATIONS

Chinese Office action for Application No. 2016108296807, dated Apr. 3, 2018, 9 pages.

(Continued)

*Primary Examiner* — Michael J Tsai
*Assistant Examiner* — Christopher E Miller
(74) *Attorney, Agent, or Firm* — Lewis Roca Rothgerber Christie LLP

(57) ABSTRACT

A therapeutic device has a bridge portion adapted for releasable adherence to a patch of skin so as to lift the patch of skin above a sensitive underlying treatment site in reducing discomfort or pain associated with tissue compression at the treatment site. The bridge portion is elevated above the treatment site with an exposed adhesive facing the patch of skin to be lifted and/or stretched outwardly. With the application of pressure to elastically deform the device from its original neutral configuration, the bridge portion is brought into contact with the patch of skin, adhering the skin to the adhesive. When the pressure is removed, the device rebounds and generally reassumes its original configuration with the bridge portion lifting the attached patch of skin.

6 Claims, 13 Drawing Sheets

Related U.S. Application Data

(60) Provisional application No. 61/685,545, filed on Mar. 20, 2012, provisional application No. 61/685,752, filed on Mar. 22, 2012, provisional application No. 61/690,106, filed on Jun. 19, 2012.

(51) Int. Cl.
| | | |
|---|---|---|
| *A61B 90/00* | (2016.01) | |
| *A61F 13/12* | (2006.01) | |
| *A61F 13/00* | (2006.01) | |
| *B29C 69/00* | (2006.01) | |
| *A61F 5/01* | (2006.01) | |
| *A61F 13/02* | (2006.01) | |
| *A61B 90/60* | (2016.01) | |

(52) U.S. Cl.
CPC .... *A61F 13/00987* (2013.01); *A61F 13/0276* (2013.01); *A61F 13/10* (2013.01); *A61F 13/122* (2013.01); *A61H 1/008* (2013.01); *B29C 69/005* (2013.01); *A61F 2013/0028* (2013.01)

(56) References Cited

U.S. PATENT DOCUMENTS

| | | | | |
|---|---|---|---|---|
| 4,212,296 A | * | 7/1980 | Schaar | A61F 13/0203 128/888 |
| 4,274,402 A | | 6/1981 | Shippert | |
| 4,285,338 A | * | 8/1981 | Lemelson | A61F 13/0203 128/889 |
| 4,664,736 A | | 5/1987 | Faasse, Jr. | |
| 4,995,114 A | | 2/1991 | Price | |
| 5,170,781 A | * | 12/1992 | Loomis | A61F 13/0203 128/117.1 |
| 5,209,718 A | * | 5/1993 | McDaniel | A61F 13/0203 128/109.1 |
| 5,213,565 A | | 5/1993 | Rollband | |
| 5,685,292 A | | 11/1997 | Fenn | |
| 5,718,224 A | | 2/1998 | Muchin | |
| 5,810,753 A | | 9/1998 | Eberbach | |
| 5,944,678 A | * | 8/1999 | Hubbard | A61F 5/0111 602/27 |
| 6,006,751 A | | 12/1999 | Spitzer | |
| 6,058,931 A | | 5/2000 | Muchin | |
| 6,065,470 A | | 5/2000 | Von Cromvoirt et al. | |
| 6,098,616 A | | 8/2000 | Lundy et al. | |
| D433,142 S | * | 10/2000 | Nash | D24/189 |
| 6,129,692 A | * | 10/2000 | Mathis | A61F 5/05866 602/12 |
| 6,155,999 A | * | 12/2000 | Bartlett | A61F 13/108 602/41 |
| 6,200,286 B1 | | 3/2001 | Zamani | |
| 6,228,101 B1 | * | 5/2001 | Stratton | A61F 5/56 128/200.24 |
| 6,315,748 B1 | | 11/2001 | Morgan, Jr. | |
| 6,375,667 B1 | | 4/2002 | Ruch | |
| 6,453,901 B1 | * | 9/2002 | Ierulli | A61F 5/08 128/200.24 |
| 6,812,374 B1 | * | 11/2004 | Wood | A61F 13/0203 128/888 |
| 7,067,710 B1 | * | 6/2006 | Beaudry | A61F 5/08 602/42 |
| 7,195,605 B1 | | 3/2007 | White | |
| 7,265,256 B2 | | 9/2007 | Artenstein | |
| 7,793,661 B2 | * | 9/2010 | Macken | A61F 5/56 128/846 |
| 8,584,671 B2 | | 11/2013 | Ierulli | |
| 2003/0125652 A1 | * | 7/2003 | Porrata | A61F 5/0118 602/21 |
| 2003/0130690 A1 | * | 7/2003 | Porrata | A61F 5/0118 606/204 |
| 2004/0049144 A1 | | 3/2004 | Cea | |
| 2005/0228323 A1 | * | 10/2005 | Tornai | A61F 5/0118 602/5 |
| 2005/0228331 A1 | * | 10/2005 | Tseng | A61F 13/105 602/58 |
| 2005/0274386 A1 | | 12/2005 | Macken | |
| 2005/0274387 A1 | | 12/2005 | MacKen | |
| 2007/0027423 A1 | * | 2/2007 | Scheinberg | A61F 13/06 602/54 |
| 2007/0255309 A1 | | 11/2007 | Bahman et al. | |
| 2007/0299383 A1 | * | 12/2007 | Murphy | A61F 13/00991 602/46 |
| 2008/0154169 A1 | * | 6/2008 | Kase | A61F 13/023 602/55 |
| 2008/0257341 A1 | | 10/2008 | Ierulli | |
| 2009/0105625 A1 | * | 4/2009 | Kohner | A61F 13/068 602/54 |
| 2009/0234383 A1 | | 9/2009 | Tornai | |
| 2012/0172779 A1 | | 7/2012 | Spinelli et al. | |
| 2012/0232455 A1 | * | 9/2012 | Beaudry | A61F 5/08 602/48 |
| 2012/0238931 A1 | | 9/2012 | Rastegar et al. | |
| 2012/0277647 A1 | * | 11/2012 | Rastegar | A61F 13/0246 602/53 |

FOREIGN PATENT DOCUMENTS

| | | |
|---|---|---|
| JP | 2005-349210 | 12/2005 |
| WO | WO 2014/126707 A1 | 8/2014 |

OTHER PUBLICATIONS

Korean Office action for Application No. 10-2014-7029249, dated Dec. 18, 2014, 4 pages.
Australian Office action for Application No. 2013235710, dated Nov. 18, 2014, 3 pages.
Australian Patent Examination Report No. 2 for Application No. 2013235710, dated May 10, 2015, 4 pages.
Japanese Office action for Application No. 2015-501683, dated May 12, 2015, 6 pages.
Chinese First Office action for Chinese Patent Application No. 201380022871.7, dated Jun. 4, 2015, 11 pages.
Extended European Search Report dated Oct. 5, 2015 for EP Patent Application No. 13764267.4-1308/2827819 PCT/US2013028099, 6 pages.
PCT International Search Report and Written Opinion for Application No. PCT/US2013/028099, dated Jun. 26, 2013, 9 pgs.
Extended European Search Report for Application No. 18184262.6, dated Oct. 25, 2018, 7 pages.

* cited by examiner

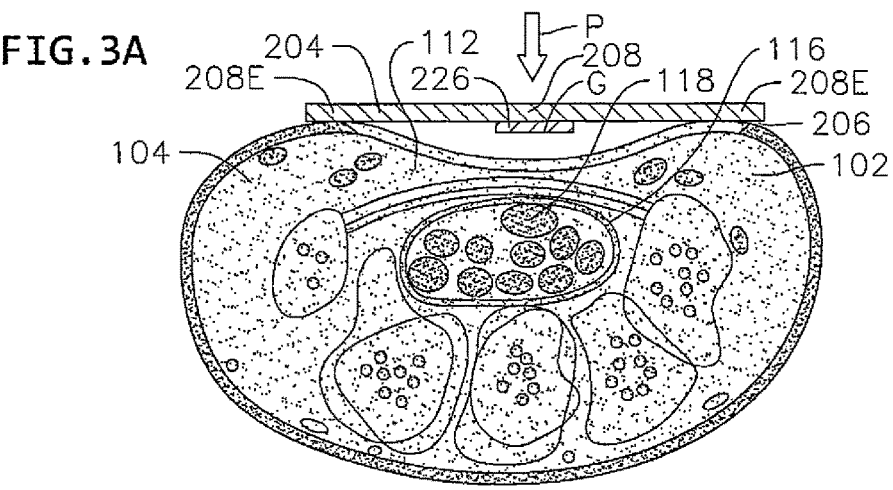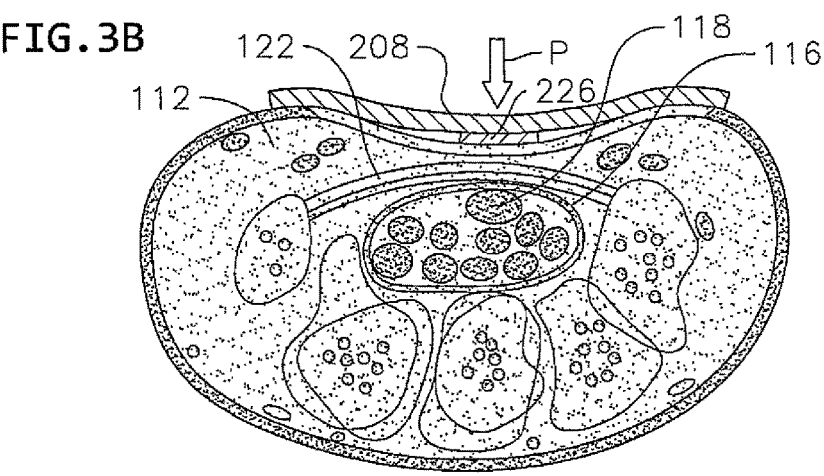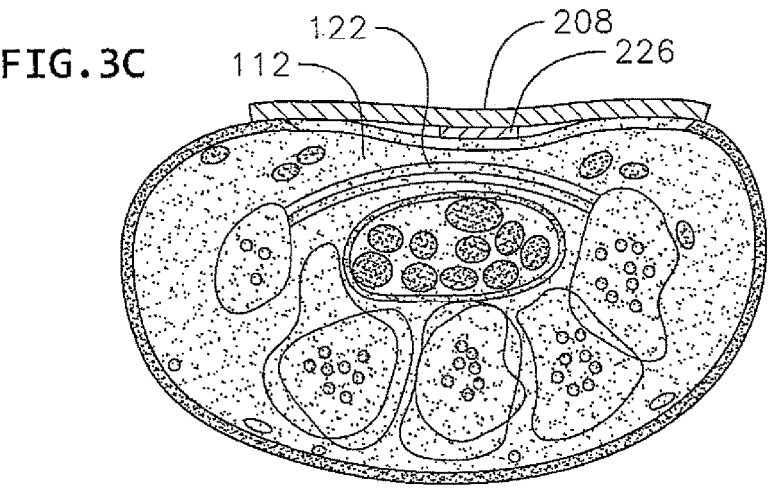

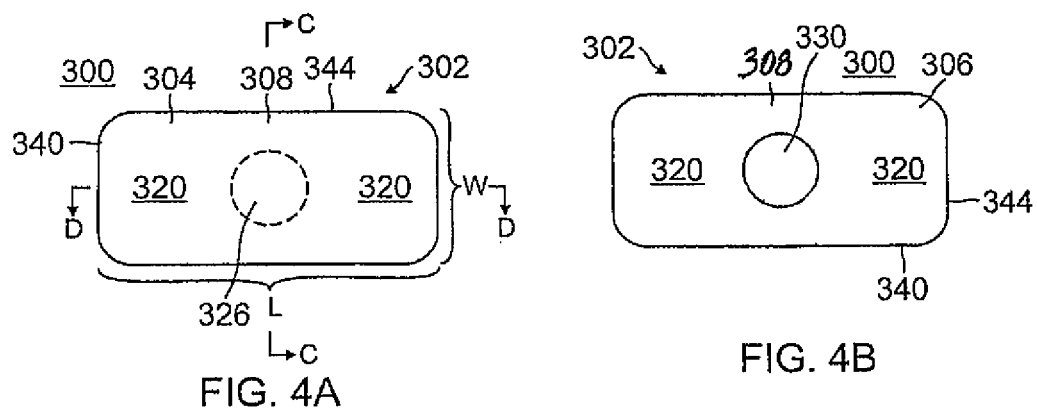
FIG. 4A
FIG. 4B
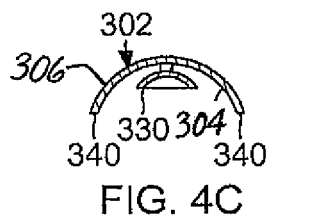
FIG. 4C
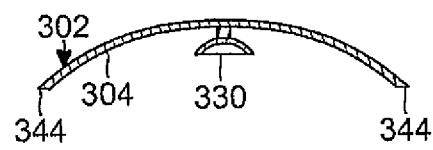
FIG. 4D
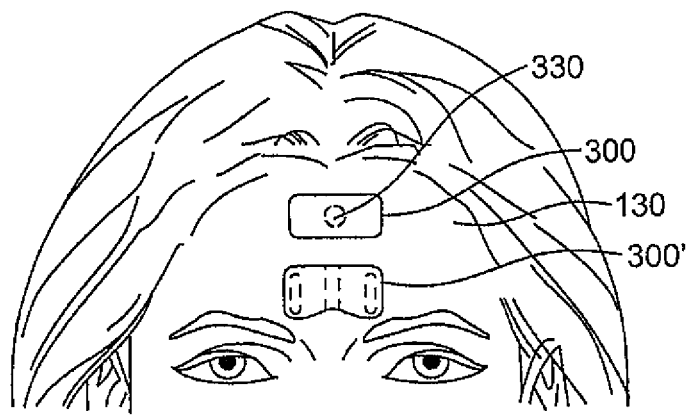
FIG. 6

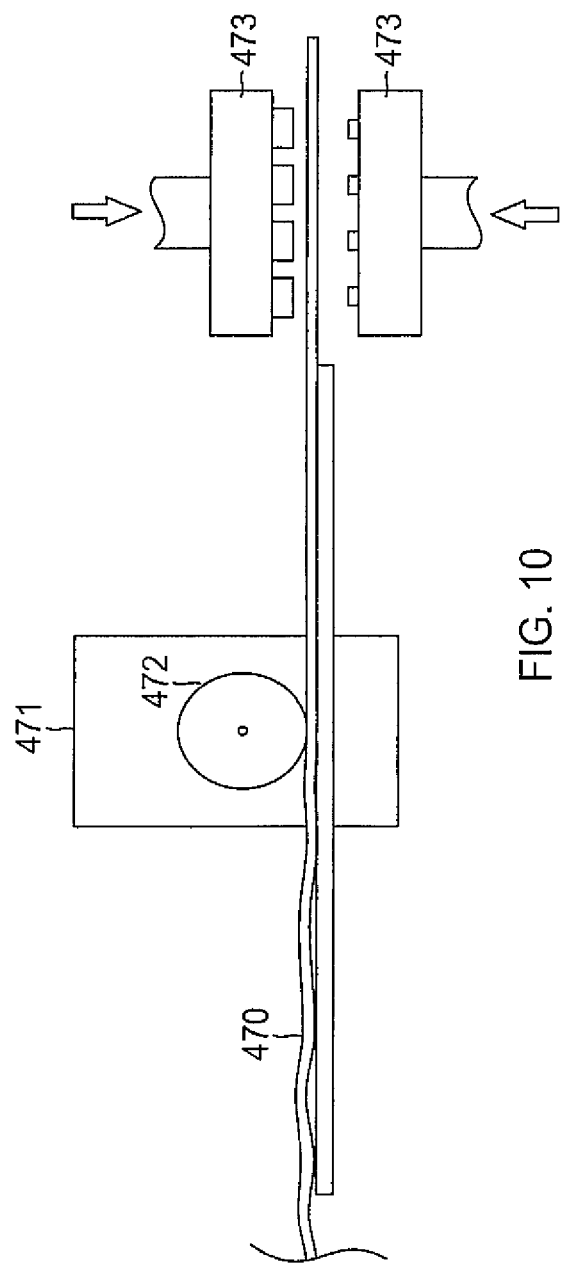

THERAPEUTIC SKIN LIFTING DEVICE AND RELATED SYSTEMS AND METHODS

CROSS-REFERENCE TO RELATED APPLICATIONS

This application is a continuation-in-part of U.S. patent application Ser. No. 13/825,759, filed on Mar. 22, 2013, which is National Phase Patent Application and claims priority to and the benefit of International Application Number PCT/US2013/28099, filed on Feb. 27, 2013, which claims priority to and the benefit of U.S. Provisional Application No. 61/685,545, filed on Mar. 20, 2012; U.S. Provisional Application No. 61/685,752, filed on Mar. 22, 2012, and U.S. Provisional Application No. 61/690,106, filed Jun. 19, 2012, the entire contents of all of which are incorporated herein by reference.

FIELD OF INVENTION

The present invention relates to a medical device for reducing symptoms of physical ailments and conditions, including pain and discomfort associated with Carpal Tunnel Syndrome (CTS), migraine headaches and other pressure-related ailments and conditions.

BACKGROUND

Carpal Tunnel Syndrome (CTS) is idiopathic median neuropathy at the carpal tunnel of a human hand. With reference to FIG. 1, a human hand 100 is illustrated with muscles in a proximate portion, below thumb 106 and pinky finger 108, including abductor pollicis brevis 102 and abductor digit minimi 104, respectively. The muscles 102 and 104 define transverse carpal arch 110 with a recess 112 therebetween that is generally aligned with third finger 114. In tissues below the recess 102 is carpal tunnel 116 where median nerve 118 enters the hand 100. This tunnel is normally narrow as it is also occupied by flexor tendons 120, so any swelling of adjacent tissue, including the flexor retinaculum ligament 122, can pinch the nerve and cause pain, numbness, tingling or weakness.

The pathology of CTS is not completely understood but can be considered compression of the median nerve traveling through the carpal tunnel. Many studies have been conducted to identify causes but the evidence is not clear. Various results published in the 1990's found strong associations between the prevalence of CTS and forceful and repetitive wrist movements such as work on keyboard and computers. However, more recent research has cited genetics and obesity as possibly larger factors than use, and has encouraged caution in ascribing causality.

Pregnant women, especially those in their third trimester, may experience hand pain and discomfort, for example, numbness, tingling sensation, or aching in the hands and wrists, particularly at night when bodily fluids are more equally distributed throughout the body and not just in the lower extremities. Because pregnancy causes swelling in many parts of the body, extra pressure may be present on the nerves in the hands and wrists, including the median nerve.

The only scientific established disease modifying treatment is surgery to cut or divide the transverse carpal ligament. However, one study found that within two years of surgery, 75% of the patients showed recurrence of pain symptoms. Moreover, surgery has many risks and is not suitable for temporary CTS, such as that experienced by pregnant women. Palliative treatments for CTS include use of night splints and corticosteroid injection. Other nonsurgical treatment methods include hand braces, exercises, ergonomic equipment, oral diuretics and nonsteroidal anti-inflammatory drugs (NSAIDs). Websites including www-.mycarpaltunnel.com discusses different treatment options. Other approaches include gloves, such as described in U.S. Pat. No. 6,006,751 and the prior art cited therein. Obviously, such gloves may be relatively expensive and are not disposable. Gloves may also limit manual dexterity and tactile sensitivity.

Kinesio tape has also been used as a nonsurgical treatment for CTS. Conventional kinesio tape is manufactured from a highly elastic strand wrapped in cotton fibers. It is employed as a gentle stretching therapy for soft tissue disorders and repetitive strain injuries. Kinesio tape has elasticity intended to match that of a person's skin, muscles, cartilage and connective fascia tissue. However, there are many different methods of taping around the hand and wrist and improper taping may cause further discomfort or even further damage to the median nerve. Moreover, proper taping often requires the use of two hands making it difficult if not impossible for a patient to apply the tape without assistance.

Hand braces and splints and temporary, removable devices worn on the hand are also known, for example, a stretching hand device described in U.S. Pat. No. 6,315,748 and sold under the mark THE CARPAL SOLUTION. The device includes a central, resilient, stretchable tensioning segment with a plurality of relatively less stretchable adhesive straps secured to the segment. In use, the segment is placed on the back of a patient's hand, whereupon the straps are pulled and adhered to the patient's palm in a fashion to expand the segment. In this orientation, the control segment exerts continuous yielding or tensile forces through the straps which in turn reduces carpal tunnel syndrome nerve compression and alleviates symptoms.

Another severe condition suffered by a significant portion of the population is migraine headaches. The pain of migraine occurs when excited brain cells trigger the trigeminal nerve to release chemicals that irritate and cause swelling of blood vessels on the surface of the brain. These swollen blood vessels send pain signals to the brainstem, an area of the brain that processes pain information. The pain of migraine is referred pain that is typically felt around the eye or temple area.

In addition to prescription and over-the-counter drugs, there are many remedies for migraines, including sleeping, taking caffeine, ice packs, and avoiding sunlight or certain foods. Kinesio tape has also been used to alleviate severe headaches. Experts believe that taping can significantly help reduce headaches by repositioning the muscles that are under stress and therefore helping to relieve tension in the neck.

Indeed, the adhesive tape or strips have many medical uses and applications beyond bandaging wounds. For example, nasal snoring strips are pieces of elastic plastic that are embedded in a sticking plaster for attachment across the outside of the nose. Shape-memory causes the plastic to straighten which effectively widens the nasal passages to allow for improved airflow. These strips are disposable and simplistic in design, construction and use.

Accordingly, there is a desire for a device that can reduce the symptoms of pressure-related conditions and ailments, including CTS and migraines. There is also a desire for the device to be simplistic in design, construction and use and be able to lift skin above a sensitive underlying site.

SUMMARY OF THE INVENTION

The device of the present invention is primarily intended for use in those suffering from Carpal Tunnel Syndrome (CTS), but also has application for relieving migraine headaches and other situations where lifting the skin and tissue above a sensitive underlying site would provide benefits.

The present invention provides for an inexpensive, reliable and easy to use device which lifts an area of skin upwardly in a direction generally perpendicular to the skin surface. It does not interfere with the sleep of the user and is a low cost disposable item. In a preferred embodiment, used for CTS, the device comprises a thin, generally rectangular member with a long dimension and a short dimension. The member is made from a plastic material, with "shape memory", which in its normal configuration is generally flat. When pressure is applied orthogonally to the member, the member deforms. When released from pressure, the "shape memory" member has spring and rebounds to its normal configuration as much as possible. On a bottom (skin-facing) surface of the device, adhesive or adhesion member (used interchangeably herein) is provided on at least part of a central portion. A removable protective cover (e.g., release liner of wax paper) is applied over the adhesive.

In use, the protective cover is removed and the adhesive is applied to the palm proximate the wrist by a force depressing the center portion of the member toward the palm and fixes the center portion of the member to the palm. The member is oriented with the long dimension of the member across the palm between the thumb and the pinky finger. Since the adhesive is applied to a concave portion of the palm, the device forms a bridge across the palm. Side portions of the member supporting the center portion are not adhered to the palm so they can slide freely in contact with the palm. The skin of the palm adhering to the adhesive of the member is pulled upwardly as a result of negative pressure when the member is released and rebounds with its "shape memory".

The adhesive can be applied to the device by any conventional means so that the adhesive remains on the member when the protective backing is removed. Alternatively, the adhesive can be applied by a user directly to the member or to the palm or skin of the user. Lifting and/or stretching the skin in the area of the palm or treatment site relieves symptoms, including the symptoms of CTS.

While a preferred embodiment envisions use of a single piece of spring-type plastic material, it is possible to incorporate other designs to provide a resilient or shape-memory member, such as synthetic whalebone, polyester boning material, metal, metal alloys, such as nitinol, and the like.

Accordingly, the present invention is directed a therapeutic device adapted for application to skin covering a treatment site on a patient's body, having a generally rigid but elastically deformable body with at least one support portion and a bridge portion, the support portion adapted to rest on the skin, the bridge portion having an adhesive adapted to adhere to at least a portion of the skin, wherein the body is adapted to assume a neutral configuration with the adhesive and the portion of the skin separated by an air gap, and an adhesion configuration with the portion of the skin adhering to the adhesive being lifted and/or stretched at the treatment site. The body is also adapted to assume a depressed configuration the wherein the body is deformed from the neutral configuration with the bridge portion being depressed to bring the adhesive into contact with the portion of the skin.

The body while in its neutral configuration supports the bridge portion at a highest elevation relative to the skin surface of the treatment site, where as the body while in its depressed configuration supports the bridge portion at a lowest elevation. Moreover, the body while in its adhesion configuration supports the bridge portion at an in-between elevation greater than the lowest elevation and lesser than the greatest elevation. The adhesive provided on an inner, skin-facing surface may include a coating or layer of adhesive material, double sided adhesive tape, at least one suction cup, and/or micro-suction cup tape.

In a more detailed embodiment, the therapeutic device has a thin sheet body with a "butterfly" configuration wherein the support portion supporting the bridge portion includes side planar portions adapted to rest on the skin. The butterfly configuration is well-suited for application to a palm of the patient's hand with the device positioned on the palm and the bridge portion longitudinally aligned with a median nerve of the palm. The adhesive is adapted for adhesion to skin below the device and above the median nerve.

The thin sheet body may also be configured rectangularly with rounded corners and one or more curved edges. As such, the device is also adapted for application on other areas of the patient's body. The rounded corners are atraumatic and the curved edge(s) accommodate features, curves and contours of the face or body, for example, nose, eyes, knuckles, elbows, knees and ankles.

In another more detailed embodiment, the therapeutic device has a thin sheet preformed body having an outer surrounding rim and a raised center bridge portion. The rim and the bridge portion may have a common shape, for example, circular, rectangular, square or polygonal. The bridge portion is supported by at least three legs extending upwardly from the rim. The preformed body is well-suited for application to a forehead, e.g., a temple region, of the patient. Each leg may be L-shaped including a radial leg portion and an axial leg portion. The radial leg portion extends between the bridge portion and the axial leg portion, and the axial leg portion extends between the radial leg portion and the outer rim.

In accordance with a feature of the present invention, the body of the device may have one or more predetermined curvatures in one or more directions. The curvature(s) serve to ensure that the bridge portion is elevated and separated from the skin below by an air gap when the device in its normal or neutral configuration. The curvature(s) also serve to strengthen the bridge portion against the pull of the adhered skin when the device has been depressed and applied to the treatment site and allowed to rebound to or toward its neutral configuration under its body's shape memory. In a more detailed embodiment, the bridge portion of the device has a curvature or concavity in at least one direction toward the inner, skin-facing surface.

The device may also be configured as a flexible band or sleeve or semi-rigid cuff to be worn on an appendage. The body is adapted to encircle or wrap around the appendage, e.g., an arm or a leg, with an inner, skin-facing surface having at least two projections or ridges with an adhesive positioned therebetween for adhesion to the skin, wherein the skin is lifted when adhered to the adhesive.

The present invention also includes a method and system for manufacturing the aforementioned therapeutic device. The manufacturing process includes:

1. A sheet of plastic material is passed through a heating tunnel to flatten or smooth the material.

2. The material is passed through rollers, for example, silicone coated rollers, to curve the material with a desired radius.

3. The material is passed through an adhesive applicator which applies adhesive, including adhesive tape, with or without a release liner.

4. The material is passed through a cutting chamber, for example a die set, which cuts bodies of the devices out of the material.

Sequence of the above steps may be varied as desired or appropriate.

The method of manufacturing may also include custom-fitting the therapeutic device by making a mold of a body part to be fitted with the device and customizing the die set to the mold.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 3A is a cross-sectional view of the therapeutic device of FIG. 2A, in a neutral configuration.

FIG. 3B is a cross-sectional view of the therapeutic device of FIG. 2A, in a depressed configuration.

FIG. 3C is a cross-sectional view of the therapeutic device of FIG. 2A, in an adhesion configuration.

FIG. 4A is a top plan view of a therapeutic device, in accordance with another embodiment of the present invention.

FIG. 4B is a bottom plan view of the therapeutic device of FIG. 4A.

FIG. 4C is a lateral cross-sectional view of the therapeutic device of FIG. 4A, taken along line C-C.

FIG. 4D is a longitudinal cross-sectional view of the therapeutic device of FIG. 4A, taken along line D-D.

FIG. 6 is a top plan view of the therapeutic devices of FIGS. 4A and 5A, as applied to a forehead of a user.

FIG. 10 is a schematic diagram of a system for implementing a method of manufacturing a therapeutic device in accordance with another embodiment of the present invention.

DETAILED DESCRIPTION OF THE INVENTION

Figure 1:
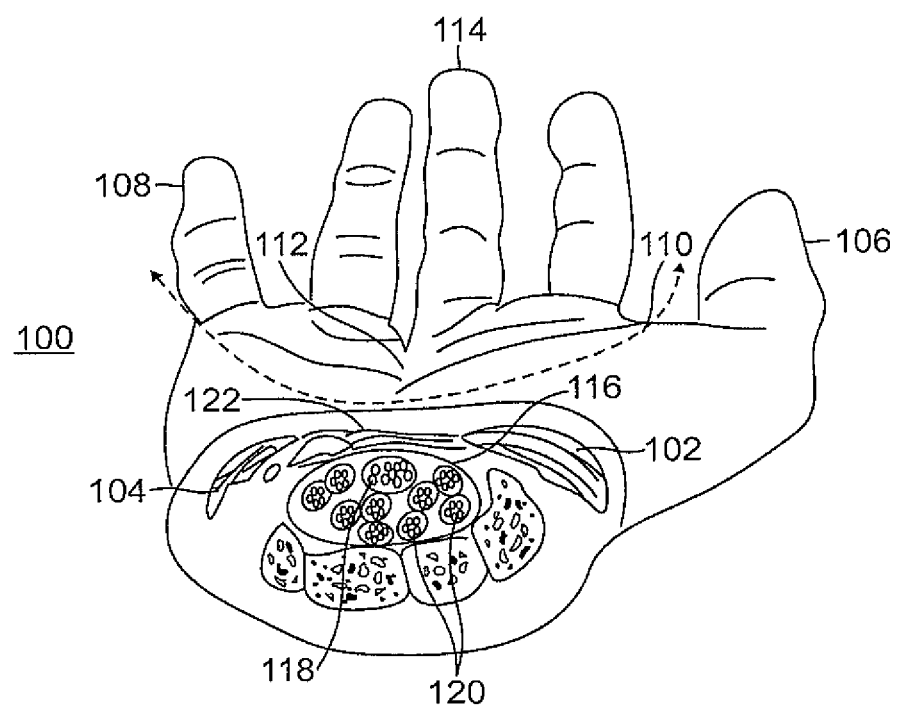
FIG. 1 is a perspective view of a hand with a cross-sectional view of a proximal portion including a median nerve and a carpal tunnel.
Figure 2A:
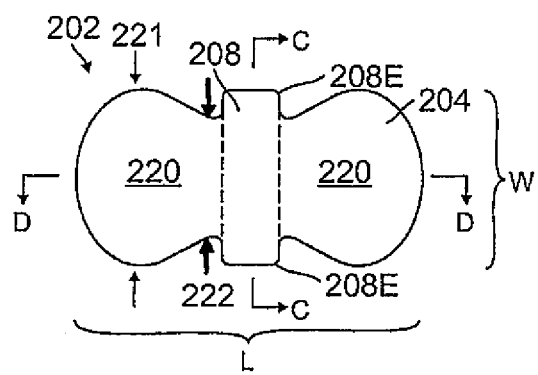
FIG. 2A is a top plan view of a therapeutic device, in accordance with one embodiment of the present invention.
Figure 2B:
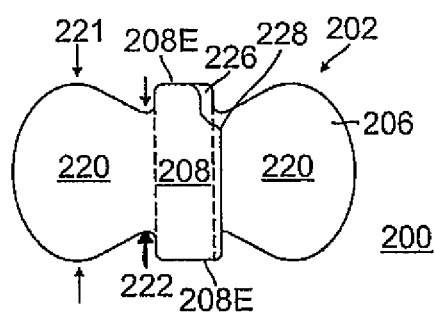
FIG. 2B is a bottom plan view of the therapeutic device of FIG. 2A.
Figure 2C:
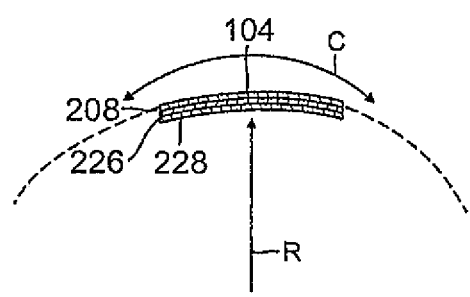
FIG. 2C is a lateral cross-sectional view of the therapeutic device of FIG. 2A, taken along line C-C.
Figure 2D:
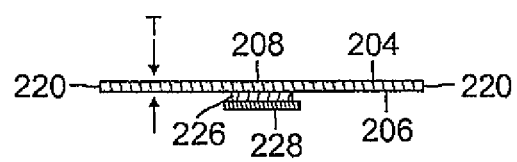
FIG. 2D is a longitudinal cross-sectional view of the therapeutic device of FIG. 2A, taken along line D-D.

The present invention is directed to a device having a bridge portion adapted for releasable adherence to a patch of skin so as to lift the patch of skin above a sensitive underlying treatment site in reducing discomfort or pain associated with tissue compression at the treatment site. The device is positioned on the patient such that the bridge portion is elevated above the treatment site in a direction generally perpendicular to the patch of skin with an exposed adhesive facing the patch of skin to be lifted and/or stretched outwardly. With the application of pressure to elastically deform the device from its original neutral configuration, the bridge portion is brought into contact with the patch of skin, adhering the skin to the adhesive. When the pressure is removed, the device rebounds and generally reassumes its original configuration with the bridge portion lifting the attached patch of skin as it returns to an elevation at or near its original elevation.

With reference to FIGS. 2A-2D, a device 200 has a thin sheet body 202 with a longer length dimension L and a shorter width dimension W. The body 202 has an outer surface 204 and an inner (skin-contacting or skin-facing) surface 206. The body 202 may be constructed of any suitable material with "memory" such that the body can be deformed under application of a force or load from an original shape or configuration and elastically return to the original shape or configuration after removal of the force or load. Depending on the underlying material of which the body 202 is constructed, the body 202 may have a thickness T ranging between about 0.012 and 0.018 inches (0.30 mm-0.45 mm), and preferably about 0.015 inches (0.40 mm). The body 202 may also be provided with one or more predetermined curvatures C, such as concavity or convexity, in one or both axes L and W.

Suitable materials for the body 102 include materials that are biocompatible or FDA-approved plastics, acrylate, polymers, metal, such as aluminum or stainless steel, or even wood or wood composites. A presently preferred material is polyethylene terephthalate (PET).

Figure 3:
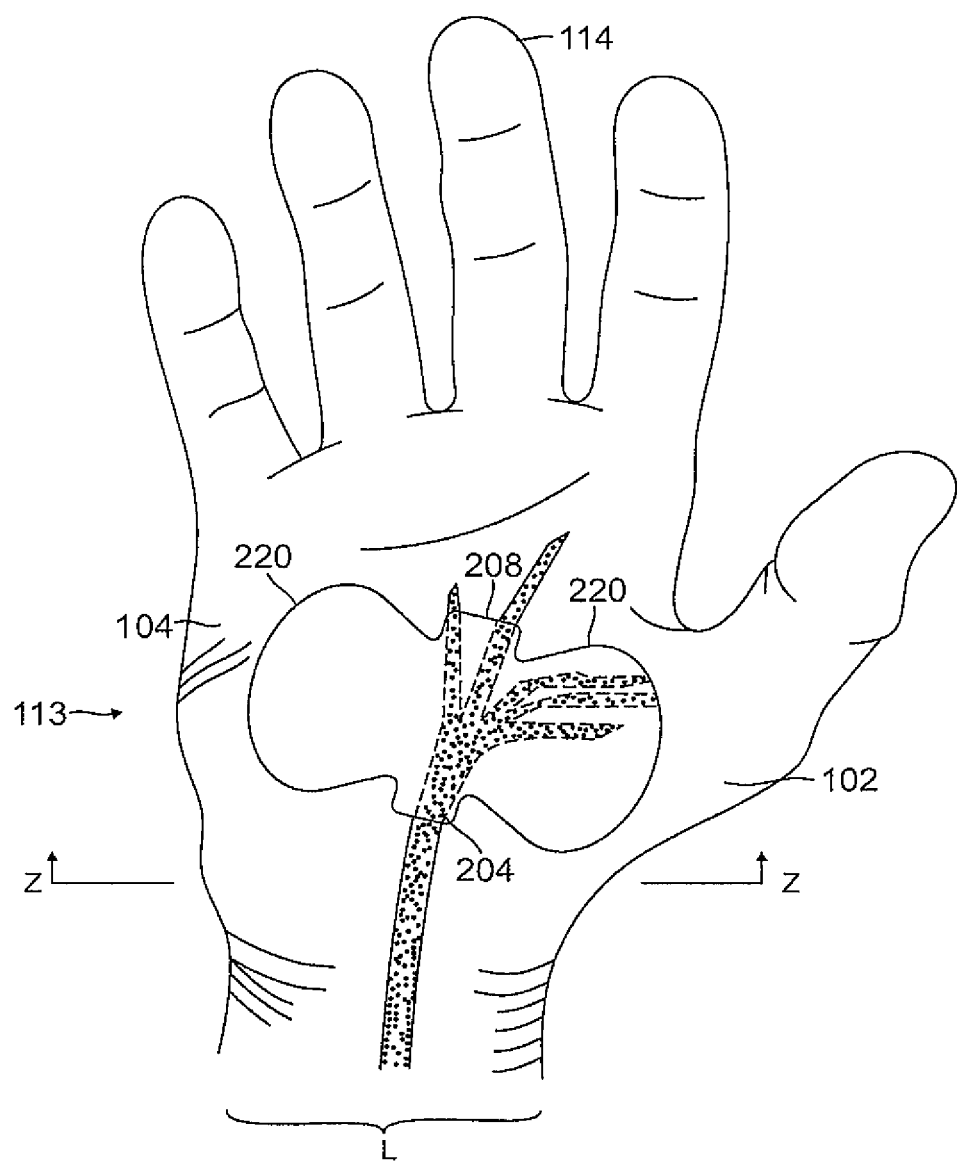
FIG. 3 is a top plan view of the therapeutic device of FIG. 2A, as applied to a user's palm.

For use of the device 200 to treat the symptoms of CTS, the thin sheet body 202 of the device has a "butterfly" configuration adapted affixation to a palm 113 of a user, as illustrated in FIG. 3. The body 202 of the device 200 has two larger side support portions or "wings" 120 and an elevated bridge portion 208 extending between the support portions 120. The body 202 spans between about 1½ inches and 1¾ inches, and preferably about 1¼ inches in the direction of the shorter/width dimension or axis W, and about 2½ inches and 2¾ inches, and preferably about 2¼ inches in the direction of the longer/length dimension or axis L.

In other embodiments, the body 202 has a thickness T ranging between about 0.012 and 0.016 inches, and spans between about 1 inch and 1⅓ inches, and preferably about 1⅕ (1.235) inches in the direction of the shorter/width dimension or axis W, and about 1⅘ inches and 2.0 inches, and preferably 1⁹⁄₁₀ (1.900) inches in the direction of the longer/length dimension or axis L.

The bridge portion 208 is rectangular, being elongated along the axis W and spanning about ⅜ inch in the L axis. Each of the side portions 220 has a rounded "petal" shape with a greater outer width 221 that tapers slightly to a lesser inner width 122 adjacent the body 208.

Moreover, the body 202 is provided with at least one predetermined curvature relative to an axis to conform to contours of the palm 113 near the wrist and location of the carpal tunnel (FIG. 1). In the illustrated embodiment of FIGS. 2C and 3, the body 202 has a predetermined concavity in the axis W toward the inner surface 206 to correspond with the convexity at the proximal end of the palm 113 (FIG. 1). The predetermined concavity of the body relative to the axis W may generally trace a circle defined by a radius R ranging between about 4 to 6 inch diameter, preferably about a 5 inch diameter.

The inner surface 206 of the bridge portion 208 is provided with an adhesion member or adhesive 226, for example, a coating or layer of adhesive for releasably affixing the device 200 to the palm. The adhesive 226 is covered and protected by a release liner 228 that is removed prior to use of the device 200 and application onto the user's skin.

With reference to FIGS. 3 and 3A-3C, use of the device 200 is described as follows. After the release liner 228 has been removed to expose the adhesive 226, the device 200 is placed over the palm 113 with the inner surface 106 and the adhesive 226 facing the palm 113. The device 200 is oriented with its longer axis L being generally transverse to middle finger 114. As shown in FIG. 3A, the device is positioned with each wing portion 220 resting on a respective convexity of the palm near muscles 102 and 104. With the device in its original and neutral configuration, the bridge portion 208 spans linearly in between the muscles 102 and 104, and elevated from the recess 112 and the median nerve 118. Advantageously, the slight but predetermined concavity of the device 100 in the lateral or W axis (FIG. 2C) enables the device to conform to the convexity of the palm 113, with the bridge portion 108 being elevated and separated from the skin below by an air gap G. As shown in FIG. 3B, to apply the device, pressure P is then applied, for example, by the user's other hand or that of an assistant, to the outer surface 204 of the bridge portion 208 above the adhesive 226 toward the skin so as to deform the bridge portion 208 (and any other portions of the body 202), bring the adhesive 226 into contact with the skin and allow the adhesive 226 to adhere to the skin, reducing or eliminating the air gap G.

When the pressure P is removed and the body 202 is released, the elastically deformable body 202 generally returns to its original neutral state in reassuming the predetermined concavity and the linearity between the bridge portion 208 and the wing portions 220, with at least a portion of the skin of the recess 112 adhering to the adhesive 226, as shown in FIG. 3C. Advantageously, the linearity or "bridging" of the bridge portion 208 when the body 202 rebounds pulls the adhered skin and adjacent tissue in the region of the recess 112 outwardly or away from the median nerve 118 to result in negative pressure and reduction of compression of the median nerve. In accordance with a feature of the invention, the lifted skin or tissue may be raised or repositioned from its original position a distance ranging between 1.0 mm to 5 mm, preferably 2.0 mm to 4.0 mm, and more preferably about 3.0 mm. To that end, the concavity of the body 202 which extends across the bridge portion 208 further strengthens the bridge portion 208 when lifting the skin against the pull of adjacent skin. Moreover, opposing ends 208E of the portion 208, each with three sides unattached to the body 102, allow the device 200 to be more flexible and comfortable while affixed to the palm, while providing additional bridging strength to the bridge portion 208 against the pull of adjacent skin, as well as providing additional surface area for the adhesive 226 to adhere with the skin.

In the disclosed embodiment, the bridge portion 208 is adhered to the skin, whereas the wing portions 220 are without adhesive and are not attached but are free to move and slide relative to the skin. This freedom of movement increases comfort to the user of the device by minimizing pinching or poking that may otherwise resulting discomfort if the wing portions (or any portions thereof) were also adhered to the skin. In that regard, a layer of fabric or liner or a coating of friction reducing gel may be provided on the inner surface of the wing portions 220 to prevent chafing. However, it is understood that the adhesive and adhesion member may be applied to one or more regions on the inner surface of the body and configured to cover beyond the bridge portion, for example, all or portion(s) of each or both wing portions 220.

It is understood that the bridge portion 208 need not be centered between the wing portions 220. That is, the size and/or shape of each wing portion 220 need not be equal or matching to the other. One wing may be larger, wider and/or longer than the other, as need or appropriate. There need not be symmetry about the axis L or W.

In an alternative embodiment of the present invention, a device 300 to treat the symptoms of a migraine headache is illustrated in FIGS. 4A-4D. Similarities between the devices 200 and 300 (as well as other devices described herein) are denoted by similar reference numerals. However, each device has different adaptations for application and affixation to the patient's body. For example, the device 300 has adaptations for application and affixation to a generally flat skin site such as forehead 130 (FIG. 6), although it is understood that the device 200 may also be used to treat migraine headaches. A body 302 of the device 300 has a generally rectangular configuration with rounded corner 340, and a bridge portion 308 contiguous with two opposing rectangular or square side support portions 320. The body 302 spans between about ¾ inches and 1¼ inches, and preferably about 1.0 inches in the direction of the shorter/width dimension or axis W, and about 2.0 inches and 2½ inches, and preferably about 2¼ inches in the direction of the longer/length dimension or axis L. The bridge portion 308 is rectangular, being elongated relative to the axis W and spanning about ⅜ inch in the L axis.

The body 302 has at least two predetermined curvatures (same or different degree of curvatures), one in the axis W (FIG. 4C) and another in the axis L (FIG. 4D), to provide concavity toward the inner surface 304 in at least two directions.

In another embodiment of the present invention for treatment of migraine symptoms, especially in the center of the forehead above the nose as illustrated in FIG. 6, a similar device 300' of FIGS. 5A-5D may have one or more arcuate longitudinal edges 342 which can accommodate placement of the device around eyes, nose or ears.

For either device 300 or 300', inner surface 206 of the bridge portion 208 is provided with adhesion member or adhesive, which may include one or more suction cups 330 (FIGS. 4A-4D) or micro suction cup tape 332 (FIGS. 5A-5D) having a surface with a multitude of microscopic craters 334 that work by creating many partial vacuums between the tape and target surface. The tape 332 can rebond repeatedly, and leaves no residue on the skin. A preferred tape is No. MSX-6800, DC Conformable Hi-Tack Type tape manufactured by 3M.

Moreover, for either device 300 or 300', on the inner surface 306 at or near lateral edges 344, each side support portion 320 includes a projection, such as a raised ridge 346 with a height H (FIGS. 5A-5B) which elevates the body 302 away from the skin so that the bridge portion 308 forms a bridge that is separated from the skin with an air gap in between. In that regard, the body 302 has sufficient rigidity to provide linearity between the portions 308 and 320. Each ridge 346 may have a different height, depending on the contour of the site. The ridges 346 may be constructed of the same material as the body 302 or of any other suitable material that provides sufficient form and structure to lift the body 302. Where the body 302 spans about 1⁷⁄₁₆ inches along the axis L, and about 1³⁄₁₆ inches along the axis W, each ridge 346 may have a thickness of about ³⁄₁₆ inch and a width ranging between about ⅛ inch and ¼ inch. Ends of each ridge may terminate a distance of about ⅛ inch from the longitudinal edges 240.

Figure 5A:
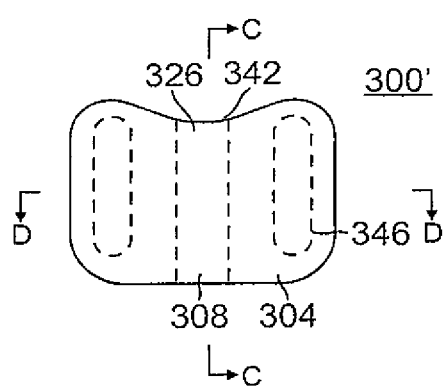
FIG. 5A is a top plan view of a therapeutic device, in accordance with another embodiment of the present invention.
Figure 5B:
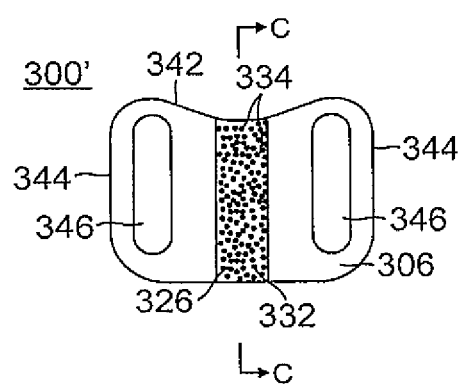
FIG. 5B is a bottom plan view of the therapeutic device of FIG. 5A.
Figure 5C:
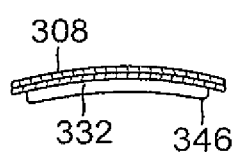
FIG. 5C is a lateral cross-sectional view of the therapeutic device of FIG. 5A, taken along line C-C.
Figure 5D:
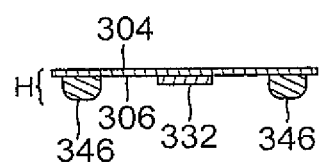
FIG. 5D is a longitudinal cross-sectional view of the therapeutic device of FIG. 5A, taken along line D-D.

It is noted that the concavity/ies of the bodies (actual or as effectuated by the ridges 346) should be of a sufficient degree such that peripheral edges, including longitudinal edges 340 and lateral edges 344 extend beyond the adhesive (e.g., adhesive coating, adhesive tape, suction cups, or micro-suction cup tape) so as to elevate the adhesive from skin and provide an initial air gap before the skin is adhered to the device (as shown in FIGS. 4C, 4D and 5D).

In use, the adhesive 326 is exposed and the device 300' is placed over the target skin site with the inner surface 306 and the adhesive 326 facing the skin. The device 300 is oriented with the ridges 346 straddling the skin site so that the bridge portion 308 and the adhesive 326 is directly over the sensitive skin site. Elevated by the ridges 346, the bridge portion 308 is situated above the skin, separated by an air gap. With the device so positioned, pressure is then applied by the user (or an assistant) to the outer surface 304 of the bridge portion 208 directly above the adhesive 326 toward the skin so as to deform the bridge portion 308 (and any other portions of the body 302), bring it into contact with the skin and allow the adhesive 326 to adhere to the skin.

When the pressure is removed and the body 302 is released, the elastically deformable body 302 generally returns to its original neutral state in reassuming the linearity between the bridge portion 308 and the side portions 320, thereby lifting the adhered skin and tissue and reducing compression at the site. The device can be situated around the eyes, near a temple, or above the nose on the forehead, as facilitated by the arcuate longitudinal edges 240, as shown in FIG. 6.

Figure 7:
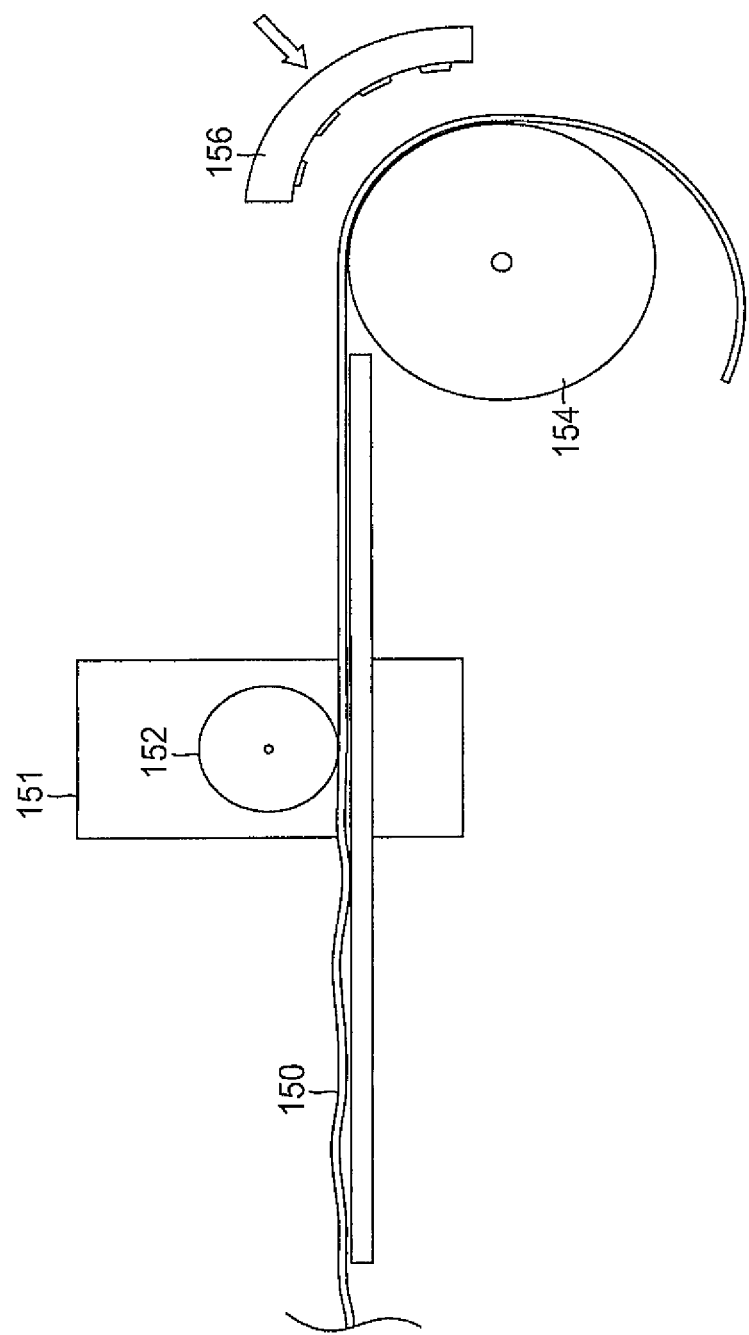
FIG. 7 is a schematic diagram of a system implementing a method of manufacture in accordance with an embodiment of present invention.

With reference to FIG. 7, the foregoing devices may be manufactured in accordance with the following method:

1. Providing a single flat sheet 150 of suitable material;
2. Heating the sheet to smooth the sheet 150 and remove wrinkles and bends;
3. Stamping, die-cutting or otherwise cutting the sheet 150 to form the device.
4. Applying the adhesive to the inner surface of the bridge portion.

The method may include forming the sheet 270 with at least one predetermined curvature.

Heating the sheet may include passing the sheet 170 through a heat tunnel 151, and/or under or between heated roller(s) 152. Forming the sheet 150 with at least one predetermined curvature may include passing the sheet through heated roller(s) 154. Stamping, die-cutting or otherwise cutting the sheet into device bodies may be performed by a die set including roller 154 and a movable punch 156. The movable punch 156 may be curved to conform to the curvature of the roller 154 to simultaneously form the device body with at least one or more predetermined curvature. Applying the adhesive 326 may occur at any stage, including before, during or after stamping, die-cutting or otherwise cutting the sheet. As mentioned, the adhesive may be medical grade adhesive suitable for topical use. It may take the form of a solid coating or layer (or a plurality of adhesive lines), double-sided adhesive tape, suction cup(s) or micro-suction cup tape. Any release liner may be applied simultaneously with the application of the adhesive or afterwards.

Where the device has ridges 246, the die set may have formations to stamp the ridges into the sheet, or they may be mounted after stamping. Alternatively, the method of manufacture may include applying or adhering the ridges 246 to the inner surface of the bridge portion before, during or after application of the adhesive to the inner surface.

Figure 7A:
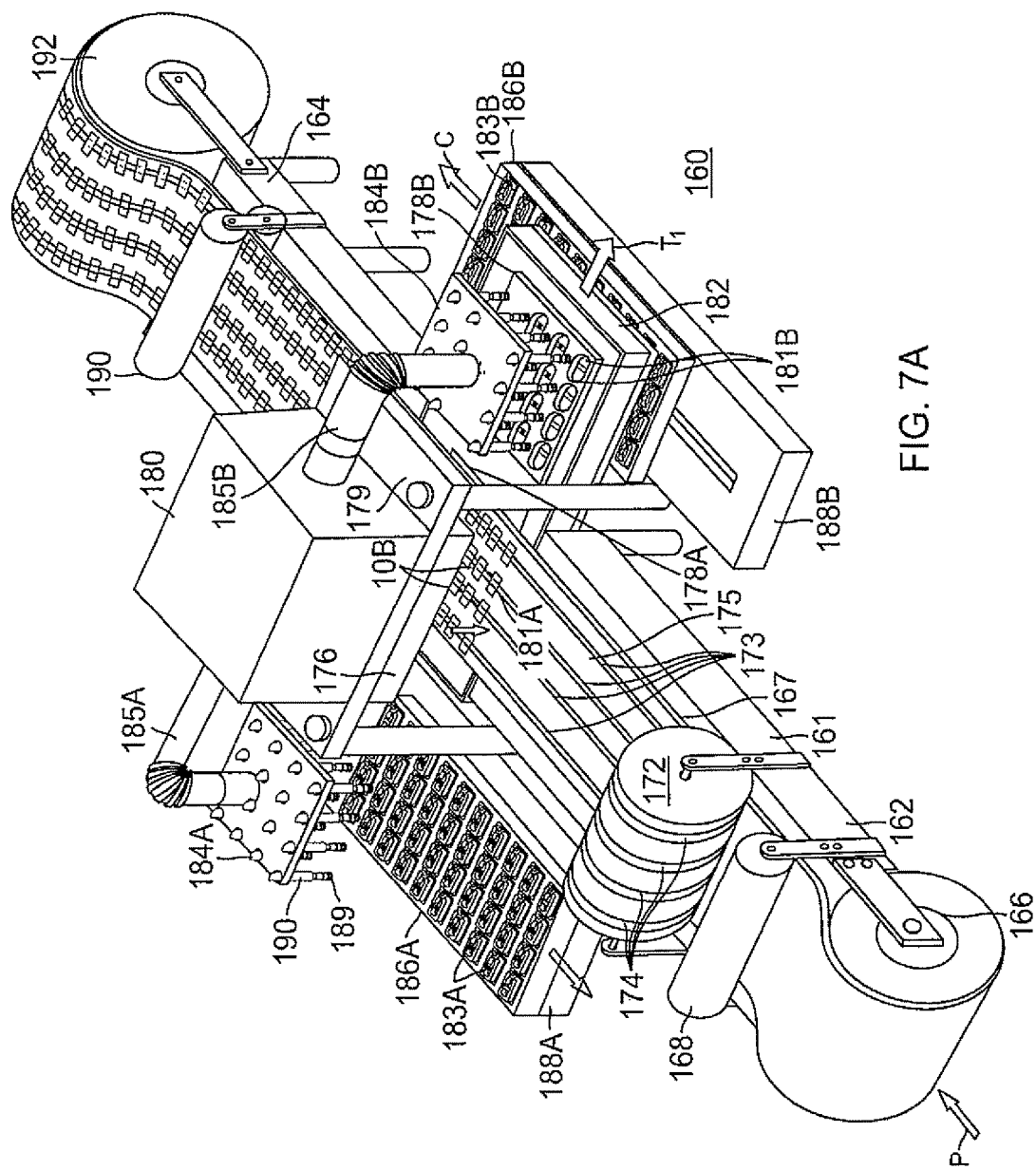
FIG. 7A is a perspective view of a machine system for manufacturing and packaging the therapeutic device of FIG. 2A, in one stage of operation in accordance with an embodiment of the present invention.
Figure 7B:
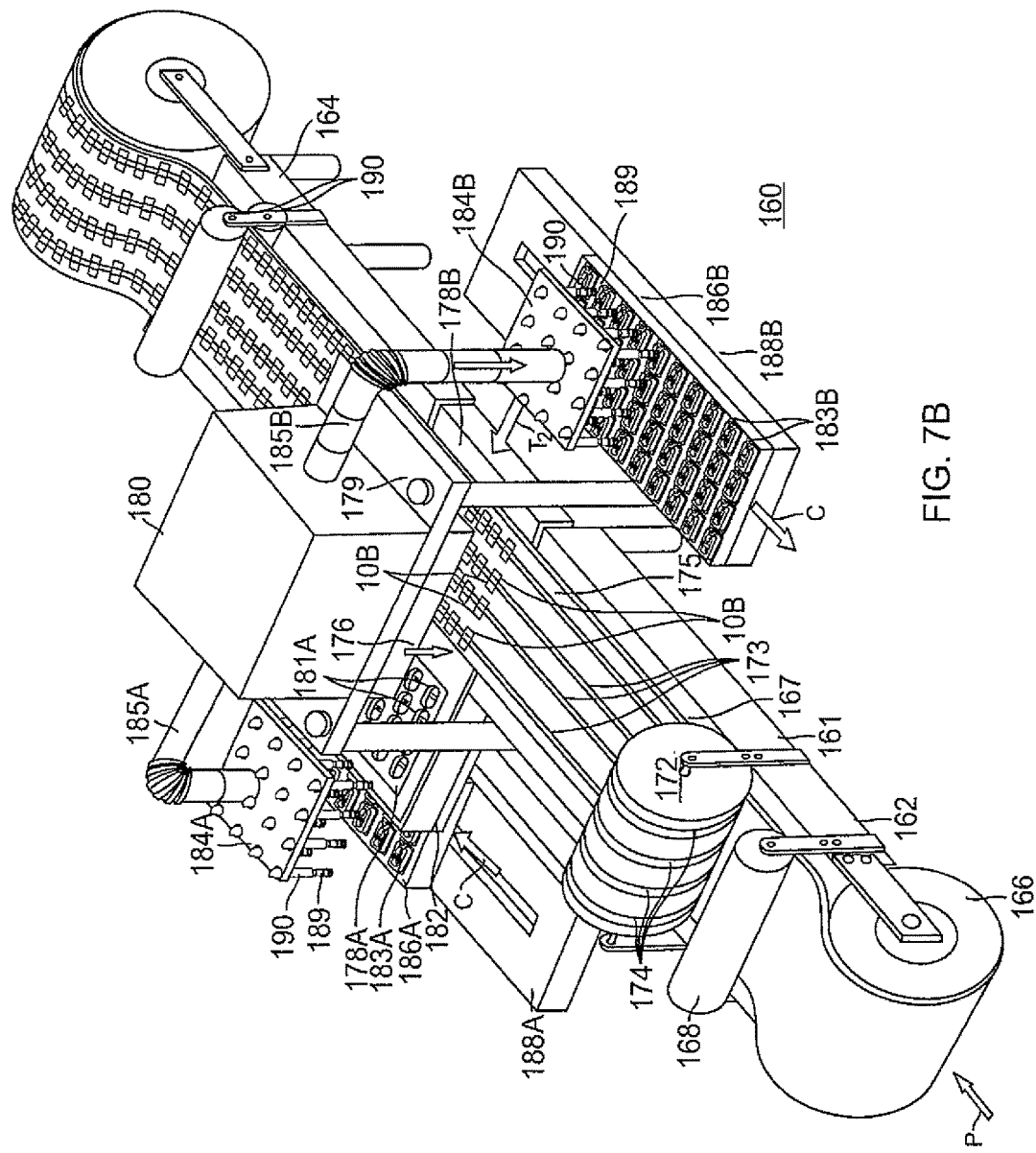
FIG. 7B is a perspective view of the machine system of FIG. 7A in another stage of operation in accordance with an embodiment of the present invention.

An embodiment of a machine system 160 implementing a method of manufacture and packaging of the device is illustrated in FIGS. 7A and 7B. The machine system 160 includes a longitudinal conveying platform 161 that defines a conveying pathway P from a first end 162 downstream to a second end 164. At or near the first end 162 is dispenser roller 166 of sheet material 167. Stored in roll form, the sheet material advantageously has a preformed curvature. To that end, the dispenser roller 166 in one embodiment of the invention has an initial diameter no greater than about 25 inches and more preferably no greater than about 20 inches.

Downstream of the dispenser roller 166 is a smooth roller 168 positioned to flatten the sheet material and remove wrinkles or bumps. Downstream of the smooth roller 168 is an adhesive tape applicator roller 172 which applies double-sided adhesive tape strips 174 onto an upward surface 175 of the sheet material (which becomes the inner/skin-facing surface of the device). The tape strips 174 are mounted on the applicator roller 172 with an exposed adhesive surface 171 facing outwardly so that it contacts and affixes to the upward surface 175 of the sheet material 167 upon pressure applied by the roller 172. Release liner strips 173 are affixed to the opposing surface of the applied tape strips 174 for subsequent removal by users when applying the devices.

Downstream of the applicator roller 172 is a die press 179 with upper platen 176 and lower platens 178A and 178B driven by air hydraulics assembly 180. The upper platen 176 is driven toward first lower platen 178A in a first stage operation of the die press and toward the second lower platen 178B in a second stage operation of the die press, as described below, to die cut a plurality of individual devices 10A and 10B from the sheet material 167 and the tape strips 174 affixed thereon.

The lower platens 178A and 178B are supported on a carrier 182 that is adapted for translational movement in opposition directions T1 and T2 along a pathway generally transverse to the conveying pathway P. In a first stage operation (FIG. 7A), the carrier 182 slides in direction T1 to position the first lower platen 178A directly below the upper platen 176 wherein the upper platen 176 engages the first lower platen 178A and cuts devices 10A in die recesses 181A, exposing the second lower platen 178B off one side of the conveying platform 161 and rendering it accessible to a transport member 184B. In the second stage (FIG. 7B), the carrier 182 slides in direction T2 to position the second lower platen 178B directly below the upper platen 176, wherein the upper platen 176 engages the second lower platen 178B and cuts devices 10B in die recesses 181B, exposing the first lower platen 178A off the opposite side of the conveying platform 161 and rendering it accessible to an opposing transport member 184A. Accordingly, the carrier 182 translates each lower platen 178A and 178B between an engagement position under the upper platen 176 and an unload position under respective a transport member 184A. Where a full die cut cycle of the die press involves the first stage operation followed by the second stage operation in sequence, the hydraulics assembly drives the die press 179 and carrier 182 in a manner whereby one of the lower platen is placed under the upper platen 176 for die cutting and while the other lower platen is exposed and accessible to a respective transport member 184. That is, in one stage of operation, the one lower platen is in the engagement position whereas the other lower platen is in the unload position, and in the other stage of operation, the other lower platen is in the engagement position whereas the one lower platen is in the unload position.

In addition to driving the die press 179 and the carrier 182, the hydraulics assembly 180 also drives support arms 185 to move the transport members 184A and 184B between at least three positions: a wait position, a load position, and an off-load position. The transport members are adapted to secure a load of devices and transport the devices from the lower platens 178A and 178B to packaging or dispensers 183 arranged on tray members 186A and 186B arranged below the lower platens in their exposed positions. As shown in FIG. 7A, when lower platen 178B is exposed and accessible to transport member 184B, the transport member 184 is actuated by the hydraulics assembly 180 to move from its wait position to the load position where it picks up devices 10B from the lower platen 178B. In the illustrated embodiment, the transport member 184 includes grippers with vacuum/suction cups 189 mounted on posts 190 which are activated to grab the devices 10B individually. With a load of devices on board, the transport member 184B is actuated by the hydraulics assembly 180 to move into the off-load position toward the tray member 186B positioned below the exposed position of the lower platen 176B and release the devices 10B into dispensers 183B. The transport member 184B is then returned to its wait position for the next cycle when the lower platen 176B contains more cut devices and is exposed and accessible again.

The tray member 186B is supported on carrier 188B which translates the tray member 186B along direction C parallel with the conveying pathway P so that the tray member 186B can shift between different positions for efficient loading of the dispensers 184. In the illustrated embodiment, the tray member is translated between two positions: a proximal position and a distal position.

It is understood that the actuation and movement of the die press 179, the carrier 182, the transport members 184A and 184B and the carriers 188 may be coordinated and synchronized with each other, as desired or appropriate for efficient operation of the machine system. For example, the upper platen 176 may be driven to engage lower platen 178A as the support arm 185B is driven to pick up devices 10B from the lower platen 178B, and as the support arm 185A is releasing devices into the dispensers 181A. A suitable system and machine for transporting work pieces is described in U.S. Pat. No. 8,230,989, entitled SHUTTLE MACHINE FOR MACHINE TOOL, the entire contents of which are hereby incorporated by reference.

The spent sheet material 167 downstream of the die press 179 is drawn downstream by a servo drive rollers 190 and collected on a waste roller 192 at the second end 164 of the conveying platform 161.

Figure 8A:
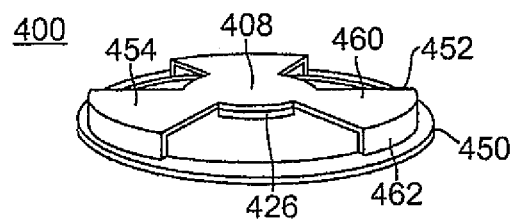
FIG. 8A is a perspective view of a therapeutic device, in accordance with another embodiment of the present invention.
Figure 8B:
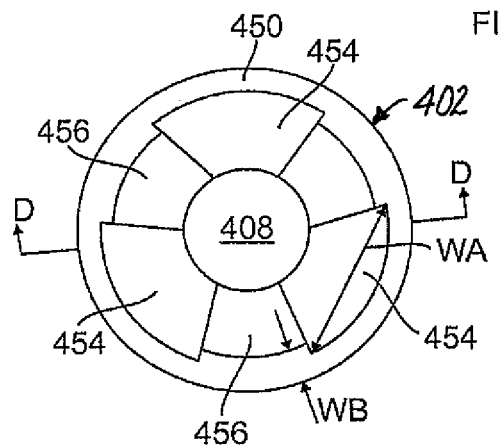
FIG. 8B is a top plan view of the therapeutic device of FIG. 8A, in a neutral configuration.
Figure 8C:
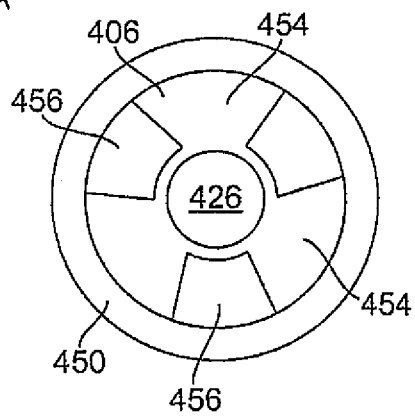
FIG. 8C is a bottom plan view of the therapeutic device of FIG. 8A.
Figure 9:
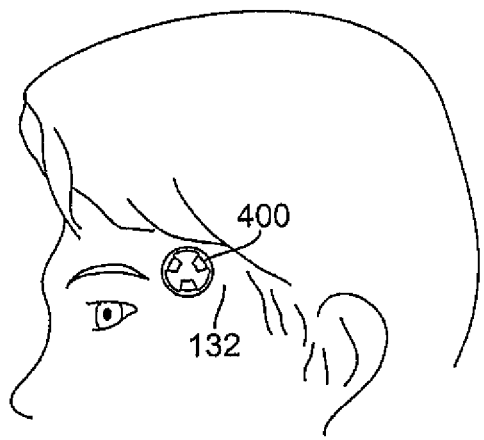
FIG. 9 is a top plan view of the therapeutic device of FIG. 8A, as applied to a temple region of a user.

Another embodiment of the present invention is illustrated in FIGS. 8A-8C. A device 400 has a thin sheet body 402 which has been formed with a raised center profile. The body 402 has a support portion 402 and an elevated planar center bridge portion 408. The support portion 402 is adapted to rest on skin above a sensitive underlying site, such as temple 132, as shown in FIG. 9. The support portion 402 includes an outer rim or base 450 and radially extending L-shaped legs or posts 454 projecting therefrom that connect the base 450 and the bridge portion 408. The base 450 is adapted to rest on and generally surround skin of a sensitive underlying site, such as temple 132, as shown in FIG. 9. Between adjacent pairs of legs is an opening 456. As better seen in FIGS. 8D-8F, each leg has a radial portion 460 coplanar with the bridge portion 408 and an axial portion 462 extending between the radial portion and the base 450. The axial portion 462 may extend at an angle ranging between about 45 to 120 degrees, preferably about 60 to 100 degrees, and more preferably about 90 degrees, from the base 450. The plurality of legs 454 ranges between about two and five.

With reference to FIGS. 8A-8F, the illustrated embodiment of the device has three legs 454 positioned equidistance from each other (e.g., centered at about 0, 120 and 240 degrees), and three openings 456. Moreover, each leg presents a 90 degree angle between the radial portion 460 and the axial portion 462, and also between the axial portion 462 and the base 450. Width of the legs can vary depending on the plurality of legs and the desired flexibility of the bridge portion 408. An inner surface 406 of the bridge portion 408 has an adhesion member or adhesive 426, for example, a coating or layer of adhesive, an adhesive tape or a micro suction cup tape, as described above. An inner surface of the rim 450 may also be provided with an adhesion member or adhesive to help secure the device on the skin.

In one embodiment, the outer radius r of the base 450 is 1.375 inches, the radius R of the bridge portion 408 is 0.5 inch, the width WA of the axial portion 462 is 0.625 inch, and the width WB of the base 450 is 0.125 inch. The height H of the bridge portion 408 from the base 450 is 0.1875 inch and the thickness of the body 402 throughout the device 10 is 0.015 inch.

The base 450 and the bridge portion 408 may each be any shape, for example, rectangular, polygonal, oval, or circular. In the illustrated embodiment, both the base and the bridge portion are circular.

Figure 8D:
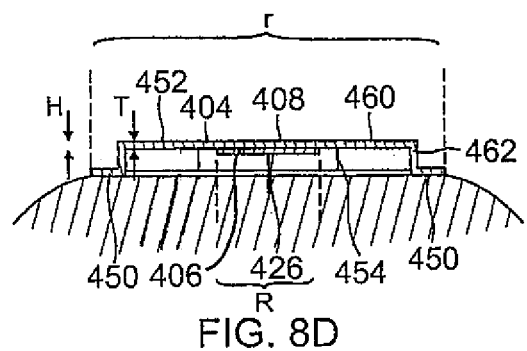
FIG. 8D is a cross-sectional view of the therapeutic device of FIG. 8B, taken along line D-D.
Figure 8E:
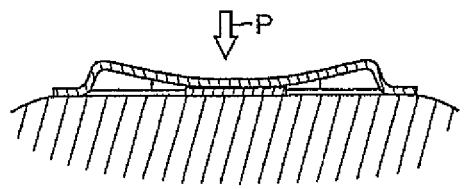
FIG. 8E is a cross-sectional view of the therapeutic device of FIG. 8A, in a depressed configuration, as applied to skin.

In use, the adhesive 426 is exposed and the device 400 is placed over the target skin site with the base generally surrounding the site and the adhesive 426 facing the skin and tissue, as shown in FIG. 8D. Elevated by the legs 454, the bridge portion 408 is situated above the skin, separated by an air gap generally equal to the height H. With the device so positioned, pressure P is applied by the user (or an assistant) to the outer surface 404 of the bridge portion 408 toward the skin so as to deform the upper body 452 (including the bridge portion 408 and/or any of the legs 454), bring the bridge portion 408 into contact with the skin and allow the adhesive 426 to adhere to the skin, as shown in FIG. 8E.

When the pressure is removed and the upper body 452 is released, the elastically deformable body 402 rebounds and generally returns to an elevation at or near its original elevation wherein the bridge portion 408 lifts the adhered skin and tissue and reducing compression at the site.

Figure 8F:
FIG. 8F is a cross-sectional view of the therapeutic device of FIG. 8A, in an adhesion configuration, as applied to skin.
Figure 8G:
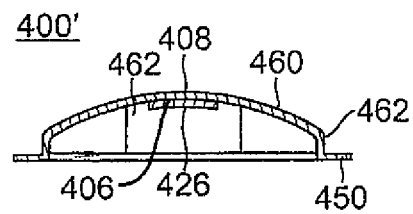
FIG. 8G is a cross-sectional view of a therapeutic device, in accordance with another embodiment of the present invention.

As shown in FIG. 8D, the bridge portion 408 and the radial leg portion 460 may extend perpendicularly relative to the axial leg portion 462, or the portions 408 and 460 may have at least one predetermined curvature in a direction. As illustrated in FIG. 8F, device 400' has an upper body 462' with curvature in more than on axial direction to provide a concavity toward the inner surface 406 that forms an elevated dome.

The devices of the present invention may be worn at all times, or only a specified time periods, such as night time, during sleep. Each device may be reused so long as the adhesive is functional. If not, the device may be discarded, or new adhesive may be applied to the device over or in place of the spent adhesive. Due to the inexpensive cost of the device and its components, the device may be economically discarded as trash or for recycling.

With reference to FIG. 10, the device 400 can be manufactured as follows:
1. Forming the device;
   (a) Injection, press or vacuum forming the base 450, bridge portion 408 and the legs 454; or
   (b) Providing a single flat sheet 470 of suitable material;
      (i) Heating the sheet to smooth the sheet 370 and remove wrinkles or bends;
         1. Heating by passing through a heat tunnel 471; and/or
         2. Heating by heated roller(s) 472.
      (ii) Stamping, die-cutting or otherwise cutting sheet to form the base 450, the bridge portion 408 and the legs 454;
         1. Die punching out the openings 456 to form the legs with die set 473;
2. Applying the adhesive 426 to the inner surface 406 of the bridge portion 408.

The stamping, die-cutting or otherwise cutting of the sheet may include both cutting of the base 450, bridge portion 408 and legs 454 from the sheet and reforming/reshaping to provide the curvature of the upper body 452 and/or angulation or bend in the leg 454 for elevating the bridge portion 408 from the base 450. The application of the adhesive 426 may occur before, during or after stamping, die-cutting or otherwise cutting of the sheet.

In yet another embodiment of the present invention, a device 500 may be worn as a band or sleeve encircling a limb or a portion thereof. With reference to FIG. 10, the device 500 is elongated defining a length axis L and a width axis W. The device 500 has a generally rigid yet flexible main body 511 having a planar, generally rectangular form, and two fastening side portions 513, each having a generally rectangular form and adjoined to an opposing side edge 515 of the main body 511. The main body 511 may be constructed of the same aforementioned suitable materials. The side portion 513 may be constructed of an elastic, stretchable material or fabric. On an inner surface 506 of the main body 511, an adhesion member 526 is provided and situated between at least two projections 546 defining an elevated bridge portion 508.

In use, the device 500 is positioned on a limb, for example, a forearm (FIG. 12), a thigh or a foot (FIG. 13), with the exposed adhesion member 526 and projections 546 facing the skin above the treatment site. The side portions 513 are wrapped around the limb and releasably fastened to each other by fasteners 517, e.g., hook and loop fasteners, eye and hook fasteners, snap fasteners, etc. The device 500 in a neutral configuration presents the bridge portion 508 at an elevated position above the skin, the two separated by an air gap. When pressure is applied to outer surface 504 of the bridge portion 508, the device assumes a deformed configuration so that the adhesion member comes 526 into contact with the skin. When the pressure is removed, the device rebounds and the skin is lifted by the bridge portion. The device 500 may have a slight predetermined curvature or concavity in the L axis toward the inner surface 506 to better conform to the limb.

Figure 12:
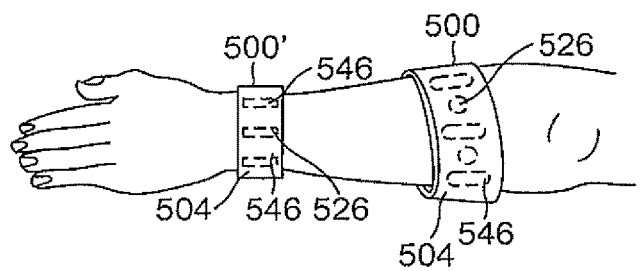
FIG. 12 is a perspective view of the devices of FIGS. 11 and 14, as applied to forearm of a user.
Figure 13:
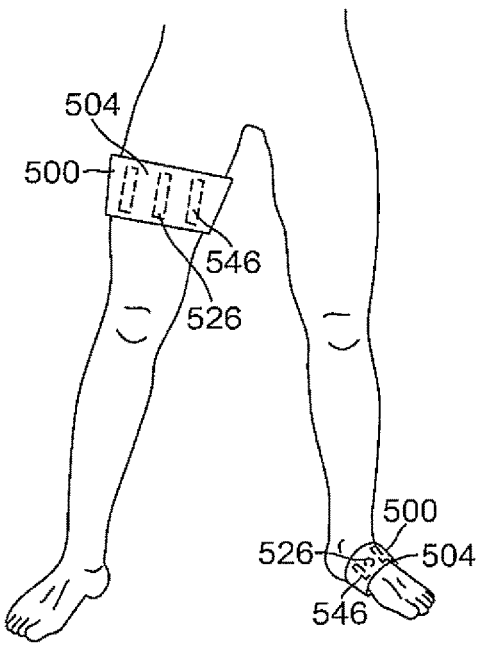
FIG. 13 is a perspective view of the device of FIG. 11, as applied to a thigh and a foot of a user.
Figure 14:
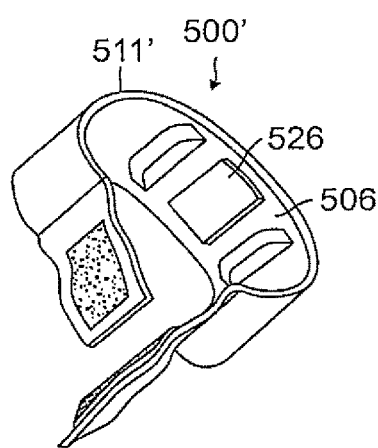
FIG. 14 is a perspective view of a therapeutic device in accordance with another embodiment of the present invention.
Figure 11:
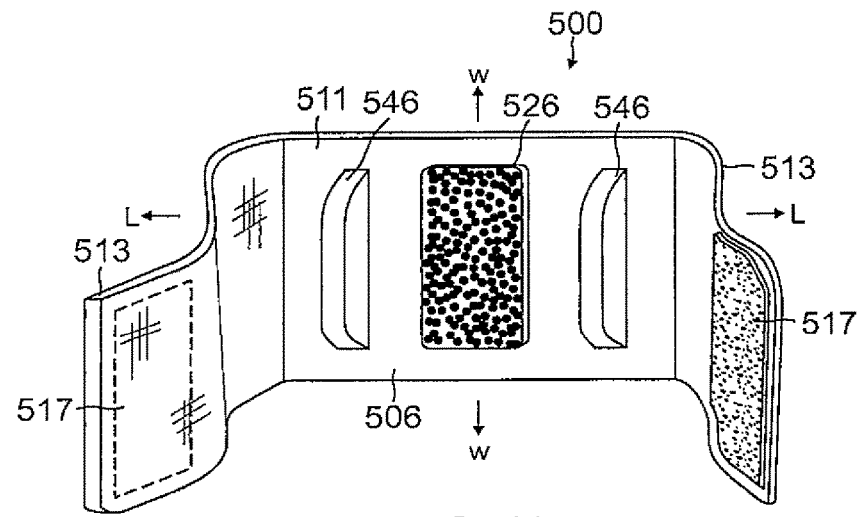
FIG. 11 is a perspective view of a therapeutic device in accordance with another embodiment of the present invention.

In a further embodiment of the present invention, a device 500' may be worn as a cuff on the wrist, as shown in FIG. 12. The device 500', as illustrated in FIG. 11, has a construction similar to that of the device 500 of FIG. 10, except that the device is smaller and has a pronounced predetermined curvature or concavity in the L axis toward the inner surface 506 to better conform to the wrist.

The present invention also includes a method of manufacturing a custom-fitted therapeutic device, wherein a mold of the treatment site, e.g., a palm, a forearm, a thigh, is made and a die set for manufacturing the device is customized according to the mold.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Dimensions of the devices may be modified to fit different sized users. As noted above, the device may have more than one adhesive or adhesive member which may be applied to different areas of the device beyond the bridge portion. Accordingly, the foregoing description should not be read as pertaining only to the precise structures described and illustrated in the accompanying drawings, but rather should be read consistent with and as support to the following claims which are to have their fullest and fair scope.

What is claimed is:

1. A therapeutic device adapted for reducing pain associated with Carpal Tunnel Syndrome by lifting skin above a median nerve in the palm of a human hand, comprising:
   a generally rigid but elastically deformable sheet body having a first surface and a second surface, the sheet body defining a longitudinal dimension and a lateral dimension, the sheet body having:

a bridge having a first surface with adhesive adapted for adhesion to skin above the median nerve in the palm; and two support wings extending outwardly from the bridge in opposite directions along the longitudinal dimension, each wing having a rounded outer free edge, wherein the bridge is narrower than each wing in the longitudinal dimension, wherein the bridge has a greater length in the lateral dimension than each of the two support wings at a junction with the bridge;

wherein a first wing of the two support wings is adapted to rest generally above a first muscle of the palm and a second wing of the two support wings is adapted to rest generally above a second muscle of the palm;

wherein the two support wings are free of adhesive; and wherein the sheet body is configured to assume a neutral configuration prior to affixation of the first surface of the bridge to the skin between the first and second muscles, a depressed position during affixation of the first surface to the skin, and an adhesion configuration after affixation of the first surface to the skin.

2. The therapeutic device of claim 1, wherein the sheet body has a predetermined concavity in the lateral dimension toward the first surface.

3. The therapeutic device of claim 1, wherein the sheet body spans between about 2½ inches and 2¾ inches in the longitudinal dimension and between about 1½ inches and 1¾ inches in the lateral dimension.

4. The therapeutic device of claim 1, wherein the bridge spans about ⅜ inches in the longitudinal dimension of the sheet body.

5. The therapeutic device of claim 1, wherein the bridge is generally rectangular with a length and a width, the length extending in the lateral dimension and the width extending in the longitudinal dimension.

6. The therapeutic device of claim 1, wherein the bridge is adapted to be positioned linearly in between an abductor digit minimi muscle and an abductor policis brevis muscle of the human hand.

* * * * *